United States Patent [19]

Cardena

[11] 4,040,187
[45] Aug. 9, 1977

[54] ORTHODONTIC ELASTIC INSERTER TOOL AND METHOD

[76] Inventor: Pedro Garcia Cardeña, Avda. de Jose Antonio No. 54, Madrid, Spain

[21] Appl. No.: 649,456

[22] Filed: Jan. 15, 1976

[30] Foreign Application Priority Data
Feb. 13, 1975 Spain ................................ 209927

[51] Int. Cl.² .............................................. A61C 7/00
[52] U.S. Cl. ........................................ 32/66; 221/297
[58] Field of Search ............... 221/290, 292, 293, 297; 32/66, 40 R, 14 A, 14 B

[56] References Cited
U.S. PATENT DOCUMENTS
3,861,045  1/1975  Canter ...................................... 32/66

Primary Examiner—Robert Peshock
Attorney, Agent, or Firm—Darby & Darby

[57] ABSTRACT

Apparatus and method for dispensing elastic members in connection with orthodontic work wherein a cartridge of such members in an undistorted shape is located between a body and a piston. The body has a tapered surface and a generally cylindrical surface. The piston slides in a sleeve, but is not rotatable therein, and a clamp engages an elastic member to move it as the sleeve is moved, over the conical surface of the body and to expand the member onto the cylindrical surface and over the same onto the device to which it is to be mounted.

11 Claims, 5 Drawing Figures

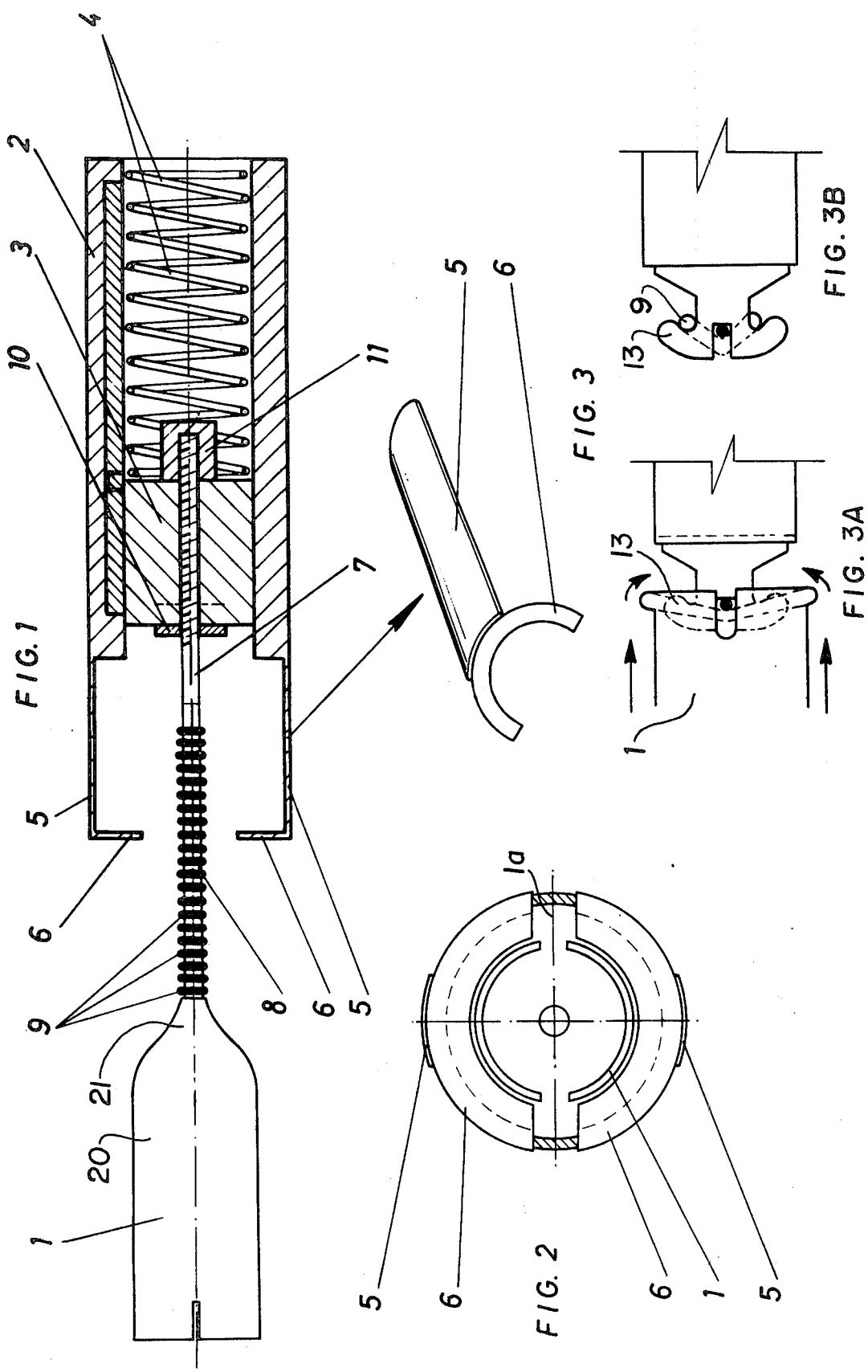

ORTHODONTIC ELASTIC INSERTER TOOL AND METHOD

The invention relates to an automatic mount for bracket arches or supports used in orthodontic work by the use of elastic rings, ligatures, staples, elastic chains or the like, as well as other type of operations carried out with certain orthodontic mechanisms, for example, giving torque or torsion, introducing and maintaining the arch inside the bracket and binding or stapling the arch to the bracket.

In applicant's Utility Model Application No. 205,180, in Spain for "APPARATUS FOR INJECTING ELASTICS, FOR ORTHODONTICS", a device is shown which consists, in essence, of a sliding link between two cylinders which are prevented from turning in their mutual fit, although sliding one on the other along their longitudinal axes. The mouths of the cylinders of the device are provided with as many notches and rectangular incisions which coincide in plan or generatrix. In the inner cylinder is fitted a cylindroconical body located so that the conical surface protrudes. The function of the conical surface is to thread, owing to its decreasing sections, the elastic rings which are to be received on the smaller cylinder.

The operation of the apparatus of the aforementioned prior application specified in the specification of the general process which is mentioned in FIG. 1 of this application and which readily can be applied to any of the earlier patent rights.

However, this prior arrangement met with some difficulties. For example, the loading times of the elastic rings were such as to make it necessary to have helpers to take care of the instrumental preparation so as to be able to leave the professional free to carry out the operation.

In Utility Model Application No. 208,057 in Spain for "APPARATUS FOR BINDING BRACKET ARCHES OR SUPPORTS BY MEANS OF ELASTICS", applicant disclosed a device which solved the disadvantage in the problem of loading, by realizing a multiple loading operation. Also, the anchoring device was modified by providing polygonal sections which were already fitted and were non-rotational but mutually sliding parts.

This improved apparatus also provided prepared loads of elastic rings by the intercalated interposition of piston type stops which permitted making a loading, which permitted and admitted carrying out a complete cycle of ligatures without requiring to reload the apparatus, reducing the operative time.

This kind of polygonal section is ideal for the final realization of disposing in the same tool of an optional set of torque or torsion wrenches by merely coordinating the mutual fit of both sleeves, outer and inner, and coinciding different types of notches of the outer sleeve with those of the inner sleeve and replacing the torsion wrenches with different notch widths without requiring to alter the rest of the device.

The sections that were tried were various ones but the greatest advantage of the octagonal, also hexagonal, was that it was possible to include the head turning mechanism and to handle different notch widths which replaced the torsion wrenches, although the rectangular or square section of rounded edges permitted the use of elastics, not only round ones but rectangular or square ones which greatly facilitated their fit in the bracket or support.

It is evident that this polygonal solution brings enormous advantages both in the results and in the mechanical and general effect of the mount, permitting to carry out innumerable successive and dependent operations with a single apparatus and a single loading, which previously required much time and handling various instruments and tools.

However, one of the greatest advantages of the mounts of the mentioned applications and which centered on the ease of having multiple loads, already sterilized and calculated for various and specific complex operations, met with the serious drawback that the constant stretch to which the elastic rings mounted and disposed in these loads were subjected caused a loss of the tonus or reduction of the elastic coefficient of the same, which made it necessary to precalculate limits of use which, although possible, notably diminished the advantage of their use.

This problem of really serious consequences for a full and normal utilization of this type of mounts, has led the applicant to slightly modify the concept of the load and, thereby, to vary the functional and mechanical structure of the mounts, as conceived before.

In accordance with the invention, the mechanical problem maintains multiple, complex or homogeneous loads, of elastic members but avoids distension beyond their critical values, which was to take place only at the time of their use, so that the short time values would not impair the elastic coefficient which the tonus would maintain in its entire construction value.

The invention therefore is designed to realize the load, by progressive distension of the elastic members only at the time of use inasmuch as the holders for the elastic members are designed to provide a loading of the elastic members thereon which fulfilled the operative conditions, but at dimensions of rest of the members, that is, without the least distension and, for this, it was necessary to modify the structure of the mount of the prior devices in a radical and important manner.

BRIEF DESCRIPTION OF THE DRAWINGS

In describing a preferred embodiment of the present invention, reference is made to the appended illustrative drawings in which:

In the drawings:

FIG. 1 shows a side elevation view in partial section of the mount according to the present invention.

FIG. 2 shows a front view of the mount; and

FIG. 3 shows a complete process of tying the elastic rings which repeats the previous processes. FIG. 3A shows the inner body portion of the mount in position for placing an elastic over the orthodontic arches. FIG. 3B shows an elastic member in position over the arches.

In the drawings there is represented by 1 the inner movable body which supports a load cartridge 8 as will be explained below. The outer body, or sleeve, 2 forms a longitudinal channel for the sliding of a piston 3 which is maintained in a certain forward position in the sleeve by the pushing action of the helical spring 4 with the spring at rest and extended. Piston 3 has a tab which rides in a slot in the sleeve 2 to prevent the turning of the piston 3 in the interior during the displacement of the outer body 2 relative to the sleeve.

The end of the sleeve 2 to which the inoperative position of the piston 3 opposite spring 4 corresponds has a flexible clamp composed by two half-moon shaped pieces whose shape and separation matches the largest outer diameter portion of the inner body 1. The half-moon shaped pieces 6 are each connected to the outer body 2 by one or more flexible tabs 5 which permit moving the half-moon pieces closer together by pressing manually by the operator on said tabs 5.

The inner body 1 is to move relative to the outer body 2. The inner body 1 is of cylindroconical shape with the cylindrical portion 20 extending away from the sleeve 2, and with the conical portion 21 inwardly. A rod 7 of relatively long length extends from the apex of the conical end of body 1. The other end of rod 7 is threaded to the piston 3 through a centered orifice thereof into a nut 11 on the other end of the piston and up to stop 10 on the first end to retain the rod and body 1 fixed to piston 3. Thus the piston 3 forms an integral unit with body 1 which is slidable along the longitudinal axis, of the sleeve 2.

The rod 7 permits and admits the threading, or stringing, of cartridges 8 on which have been directly disposed the elastic rings 9 on the releasable rod without the distortion of the rings. The rings are thus able to be stored indefinitely without danger of loss of the tonus or reduction of the coefficient of elasticity. The cartridges 8 can be a body and attached rod 7 over which the rings have been placed; the rod itself which can be made releasable from both the body 1 and piston 3; or a section of the rod 7 which can be detached from the rest of the rod and then reattached, for example, by threading. In each case the elastic rings 9 are held on a member which is of an outer diameter so as not to distort the rings, i.e. the rings are not stretched.

It will be understood that these forms of the cartridges 8 are stated by way of example, and that other variations may be used as desired by the orthodontist or other user. The rings can be of diverse colors shapes, elasticities, and other characteristics to accommodate the different purposes and order of insertion and use and with the full assurance that mechanical and elastic conditions would not be lost in storage. As explained before, the cartridges 8 would thread easily and simply on the rod 7 of the inner body 1 the end of whose rod 7 would introduce itself in the central orifice of the piston 3 of the outer body 2 up to the stop 10 and screwing the nut 11 at its protruding threaded end, so that the body 1 forms an integral unit with the body 2. In use, as shown in FIGS. 3A and 3B, the operator places a hollow end of body 1 over a bracket 13 of the device to which a ring 9 is to be attached. The bracket 13 has an arch 16 with a slot 17 through which a device to be fastened, such as a wire 14, passes. The mouth of the body 1 is hollow with a slot 1a to accommodate the wire. The interior of the mouth of the body also can be shaped to accommodate any shape of bracket and arch and also to act as a wrench for turning the same. That is, the sleeve 2 can be turned by the operator to turn the bracket or arch since the piston 3 and body 1 will not rotate relative to sleeve 2. The operator will then pinch the tabs 5 which bend to close the clamp of the half-moon pieces 6 on the outer surface of the cartridge 8 in back of the ring 9 on the cartridge nearest the conical portion 21. By pushing the sleeve 2 forwardly toward the inner body 1 the first ring 9 is moved and forced to expand slowly over the conical surface 21 of body 1 and then over its cylindrical surface 20 as is illustrated in FIG. 3. The pushing is continued until the elastic ring 9 moves off body 1 to embrace the bracket 13 and to fasten over the arch thereon to hold the wire 14. At this time the pushing action of the spring 14 moves the piston 3 back to its initial position and permits repeating the entire cycle.

As is easily deduced, the progressive action of this operation can be carried out without the least interruption, and the professional can select the first ring 9 by pinching the flexible tabs 5 at the end of sleeve 2, mount it on the body 1, continue to push and to cause the half-moon pieces 6 to push the ring 9 to engage over the bracket 13 and to fasten the arch, all in a continuous manner, without the least interruption. A complete set of rings disposed in the cartridge for one operation will avoid the loss of time due to loading operations. Also, the rings keep their original elasticity during storage thereof due to their unflexed storage position.

Changes in the specific embodiment used may be made without departing from the essence of the invention. For example, the inner section through which the piston slides may use any suitable means, in order to prevent the mutual turning with respect to the sleeve 2. The shape of the pieces 6 may be of any suitable shape as may be the nature and form of the flexible tabs. Similarly, the number and location of the notches 1a made in the mouth of the inner body are made to coincide with the separation of the pieces 6 to permit the force needed to force the rings over the arches before fitting in the brackets. Of course, the device can be constructed of any dimensions and materials.

What is claimed is:

1. Orthodontic elastic inserter apparatus comprising:
a hollow sleeve having an opening;
piston means mounted and slidable within said sleeve, said piston means adapted to support storage means;
storage means attached at one end to said piston means and passing longitudinally through said opening, said storage means adapted to pass through said elastic rings;
a body attached to the other end of said storage means and having a tapered surface adjacent said storage means, said surface adapted to receive said elastic rings annularly, and
flexible clamp means, mounted to said sleeve and proximate said storage means, for engaging a selected one of said elastic rings on said storage means, whereby said selected elastic ring expands by movement of said tapered surface through said selected ring.

2. Apparatus as in claim 1 wherein said elastic members comprise rings and said storage means is a rod over which said rings fit in a substantially undistorted condition.

3. Apparatus as in claim 2 wherein the portion of said body connected to the storage means has a tapering transition section adjacent the storage means to aid in placing said rings on said body.

4. Apparatus as in claim 3 wherein said clamping means comprises a pair of clamp members, each having a corresponding flexible member connecting each said clamp member to said sleeve, each said clamp member having an inner surface shaped to conform to a part of the outer surface of said body to permit it to pass thereover.

5. Apparatus as in claim 1 further comprising means for mounting said piston means within said sleeve to prevent rotation of the piston means relative to the sleeve.

6. Apparatus as in claim 5 further comprising resilient means for biasing said piston means in a direction outwardly toward said opening of said sleeve.

7. Apparatus as in claim 1 further comprising means for detachably mounting said storage means to said piston means.

8. Apparatus as in claim 7 wherein said elastic members comprise rings and said storage means is a rod over which said rings fit in a substantially undistorted condition.

9. Apparatus as in claim 5 further comprising means on said body for locating the same relative to a member to which an elastic means is to be attached in a fixed position as the sleeve is moved longitudinally of the body to prevent rotation of the body.

10. Orthodontic elastic inserter apparatus comprising:
a cylindrical housing defining a cylindrical inner chamber having one closed end and an opposing open end, said chamber adapted to slidably receive a sliding member;
a spring disposed within said chamber adjacent said closed end and extending at least partially and axially along said chamber;
a sliding member slidably mounted within said chamber and disposed for movement toward said closed end against the urging of said spring;
stopping means disposed within said housing for preventing sliding movement of said sliding member beyond a predetermined point in the direction urged by said spring;
an elongate rod mounted to said sliding member and axially within said housing, said rod passing through said open end of said chamber when said sliding member abuts said stopping means, said rod being adapted to pass through said rings and having a circumference to permit rings of a predetermined size to be stored on said rod without substantial expansion of said rings;
a delivery member axially mounted to the end of said rod opposite said sliding member, said delivery member having an inner portion adjacent said rod and there having its minimum diameter substantially equal to the diameter of said rod, said delivery member also having an outer portion having a diameter larger than said diameter of said inner portion, said inner portion and said outer portion being joined by a tapered and substantially continuous surface; and
a pair of opposing clamps each mounted to said housing at said open end by a pair of opposing flexible members, each of said clamps having substantially the shape of one-half of a ring, the innermost surfaces of each of said clamps being adapted to engage a selected one of said rings and to support said rings throughout relative movement of said delivery member towards said closed end of said central opening, said clamps adapted to admit said delivery member between said clamps during said relative movement.

11. A method for storing and delivering elastic rings to a predetermined position on orthodontal braces comprising:
engaging a selected ring stored on a storing member passing through said ring;
moving said ring annularly over a surface having a gradually increasing tapered surface, thereby disposing said ring at a delivery position; and
moving said ring beyond said delivery position.

* * * * *